US 11,680,894 B2

United States Patent
Wyatt et al.

(10) Patent No.: US 11,680,894 B2
(45) Date of Patent: Jun. 20, 2023

(54) LOCAL AND GLOBAL PEAK MATCHING

(71) Applicant: MLS ACQ, Inc., East Windsor, CT (US)

(72) Inventors: Eddie Dean Wyatt, Havertown, PA (US); Martin L. Spartz, Ellington, CT (US)

(73) Assignee: MLS ACQ, INC., East Windsor, CT (US)

( * ) Notice: Subject to any disclaimer, the term of this patent is extended or adjusted under 35 U.S.C. 154(b) by 0 days.

(21) Appl. No.: 17/555,803

(22) Filed: Dec. 20, 2021

(65) Prior Publication Data
US 2022/0113249 A1 Apr. 14, 2022

Related U.S. Application Data

(62) Division of application No. 16/115,178, filed on Aug. 28, 2018, now Pat. No. 11,237,101.

(60) Provisional application No. 62/551,936, filed on Aug. 30, 2017, provisional application No. 62/551,933, filed on Aug. 30, 2017.

(51) Int. Cl.
| | |
|---|---|
| *G01N 21/3504* | (2014.01) |
| *G01N 30/02* | (2006.01) |
| *G01N 30/86* | (2006.01) |
| *G01N 33/00* | (2006.01) |
| *G01N 21/35* | (2014.01) |
| *G01N 30/04* | (2006.01) |
| *G01N 30/72* | (2006.01) |

(52) U.S. Cl.
CPC ......... *G01N 21/3504* (2013.01); *G01N 30/02* (2013.01); *G01N 30/8668* (2013.01); *G01N 30/8672* (2013.01); *G01N 30/7206* (2013.01); *G01N 33/0047* (2013.01); *G01N 2021/3595* (2013.01); *G01N 2030/025* (2013.01); *G01N 2030/042* (2013.01)

(58) Field of Classification Search
CPC ............... G01N 30/02; G01N 30/7206; G01N 30/8668; G01N 30/8672; G01N 21/3504; G01N 33/0047; G01N 2030/025; G01N 2030/042; G01N 2021/3595
USPC .......................................................... 702/24
See application file for complete search history.

(56) References Cited

U.S. PATENT DOCUMENTS

| | | | |
|---|---|---|---|
| 4,802,102 A | 1/1989 | Lacey | |
| 6,555,821 B1 * | 4/2003 | Himberg | G01N 21/3504 250/339.08 |
| 9,606,088 B2 | 3/2017 | Spartz et al. | |
| 9,812,306 B2 | 11/2017 | Andersson et al. | |
| 10,656,128 B2 | 5/2020 | Wyatt et al. | |
| 2011/0054804 A1 | 3/2011 | Pfaff | |

(Continued)

FOREIGN PATENT DOCUMENTS

| | | |
|---|---|---|
| EP | 2541585 | 1/2013 |
| JP | 63-82346 A | 4/1988 |

*Primary Examiner* — John H Le
(74) *Attorney, Agent, or Firm* — HoustonHogle LLP

(57) ABSTRACT

A process for identifying an unknown compound in a sample includes matching a peak in a primary Fourier Transform Infrared spectral region of the sample spectrum with reference spectra in the same spectral region to generate an initial list of potential candidates, based, for example on goodness of fit criteria. The initial list can be reduced by retention time information and/or global peak matching techniques that analyze the sample spectrum in regions outside the primary region.

19 Claims, 10 Drawing Sheets

(56) References Cited

U.S. PATENT DOCUMENTS

| | | |
|---|---|---|
| 2014/0297201 A1 | 10/2014 | Knorr et al. |
| 2015/0260695 A1 | 9/2015 | Spartz et al. |
| 2017/0122920 A1 | 5/2017 | Spartz et al. |
| 2017/0299559 A1 | 10/2017 | Wyatt et al. |
| 2018/0045694 A1 | 2/2018 | Wyatt et al. |
| 2019/0064131 A1 | 2/2019 | Wyatt et al. |

* cited by examiner

| Gas | Visual Fit | Goodness of Fit |
|---|---|---|
| Acetamide- N-N-dimethyl- [127-19-5] |  | 0.95562 |
| Phenol [108-95-2] |  | 0.94583 |
| Benzaldehyde [100-52-7] |  | 0.50368 |
| Isothiazole- 4-phenyl- [936-46-9] |  | 0.25008 |

Local Region Filtering Step

LOCAL AND GLOBAL PEAK MATCHING

RELATED APPLICATIONS

This application is a Divisional of U.S. patent application Ser. No. 16/115,178, filed on Aug. 28, 2018, which claims the benefit under 35 USC 119(e) of U.S. Provisional Application No. 62/551,936, filed on Aug. 30, 2017, and is related to U.S. Provisional Application No. 62/551,933, filed Aug. 30, 2017, all of which are incorporated herein by reference in their entirety.

BACKGROUND OF THE INVENTION

Fourier transform infrared (FTIR) spectrometry can be a rapid and sensitive technique often used in the identification of molecular species present in a sample. Typically, the technique measures the absorption of infrared radiation by a material as a function of wavelength or frequency. The infrared (IR) absorption bands (also referred to as "peaks" or "features") observed can identify molecular components and structures.

In the laboratory or in the field, FTIR instrumentation can be part of a larger system, a system that can include, for example, a gas chromatography (GC) apparatus.

Gas chromatography (GC) is an analytical approach for separating chemical substances based on differences in partitioning behavior between a flowing mobile phase (gas phase) and a stationary phase supported in a column to separate the components in a mixture. As the gas flow passes through the column, the sample components move at velocities that are influenced by the degree of interaction of each component with the stationary phase in the column. Consequently, the different components separate as the components elute from the column.

While GC can be used to resolve a mixture into its various components according to retention profiles of the different molecules passing through the GC column, and can potentially handle mixtures containing large numbers (hundreds, for instance) of substances, identifying the molecules that elute from the column is more problematic. For example, full peak separation is often needed to qualify and quantify compounds present. Small sample sizes and dynamic ranges, and the need for continuing calibration are additional drawbacks.

A Gas Chromatography-Fourier Transform Infrared Spectrometry (GC-FTIR) system can address some of the above-mentioned problems and provide a powerful sample analysis tool.

Nevertheless, historically the designs of GC-FTIR instrumentation have been plagued with their own limitations. For example, many GC-FTIR sample cells utilize a "light pipe" (typically a cell or cuvette used for passing both gas eluted from the GC column, and light from the FTIR interferometer). The light pipe is made relatively short to prevent peak dilution through the IR cell and its eventual IR detection or secondary detection. Since IR absorption is proportional to cell path length, this short path length limits the sensitivity (minimum detection limit (MDL)) of the technique. Problems also arise in cases in which GC peaks come off very quickly. Since the light pipe has a relatively large volume when compared to the flow rates of the GC, the gas can become diluted, making measurements more difficult.

More recently, Spartz, et al., in U.S. Pat. Appl. Pub. No. US 2015-0260695 A1, now U.S. Pat. No. 9,606,088, issued Mar. 28, 2017, both of which are incorporated herein by this reference in their entirety, disclose GC-FTIR techniques and systems with the objective of coupling existing or newly developed approaches, such as GCs, and/or optical spectroscopy systems (e.g., FTIRs) in ways that reduce or minimize the deficiencies encountered with conventional arrangements.

SUMMARY OF THE INVENTION

The invention generally relates to methods for analyzing samples, for instance samples that contain more than one of unknown compounds (also referred to herein as "unknown substances", "unknown gases", "unknown vapors" or simply "unknowns"). In many of its embodiments, the invention relates to identifying likely unknown substances based on the peaks in the sample spectrum.

Peak features that appear in a sample FTIR spectrum are caused by compounds absorbing IR light. These peaks are indicative of one or more substances (often in gaseous or vapor form, "gas" and "vapor" being used herein interchangeably) being present in the sample. When analyzing a spectrum, a technician may not know from the onset what specific unknowns may be present in the sample. Thus, a need exists for computer analysis techniques that can be utilized to identify likely gases based on the peaks in the sample spectrum.

In one of its aspects, the invention features an automated process for identifying an unknown compound in a sample. The process includes a computer system comparing a peak in a primary spectral region of the sample spectrum with reference spectra for the same region to obtain an initial list of potential candidates. The initial list of potential candidates is further reduced by a global peak matching method in which reference and sample features outside the primary spectral region are compared by the computer system to obtain a reduced list of candidates. Criteria used to obtain the reduced list include the following: whether the sample has a corresponding peak for the reference spectrum; and whether the reference peak extends outside the sample spectrum. In some implementations, the initial list of potential candidates is filtered by retention time data by the computer system.

In one embodiment, a process for identifying an unknown compound in a sample, using a chromatography and spectrometry system, includes: selecting a primary FTIR region such as a computer system enabling the selection via a user interface; the computer system performing a regression analysis on sample spectral features and reference spectral features in the primary region to generate a goodness of fit metric; applying a first goodness of fit threshold value to generate a list of potential candidates; identifying a reference peak in a second FTIR spectral region that is outside of the primary FTIR region; performing a second regression analysis to generate a second goodness of fit metric for comparing the reference peak in the second FTIR spectral region with a corresponding spectral peak in the spectra of the potential candidates; and the computer system eliminating from the list of potential candidates those candidates for which a second goodness of fit is below a second threshold value and those for which the reference spectrum peak, scaled by a regression coefficient, is greater than the corresponding spectral peak in the spectra of the potential candidates.

Practicing embodiments described herein can result in the identification of unknown compounds, such as, volatile organic compounds, for instance, present in a sample. Even if some of these unknowns are not of direct interest, identifying them and including their spectra in regression operations is likely to improve the accuracy of computing concentrations for the gases of interest and identifying other unknown substances in a sample that may be of interest.

Global peak matching can reduce the number of recommended gases the end user has to search through to identify unknowns in the system. Reducing the candidate search lists saves the end user time and may lead to more accurate identification of unknowns in the sample.

The above and other features of the invention including various details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
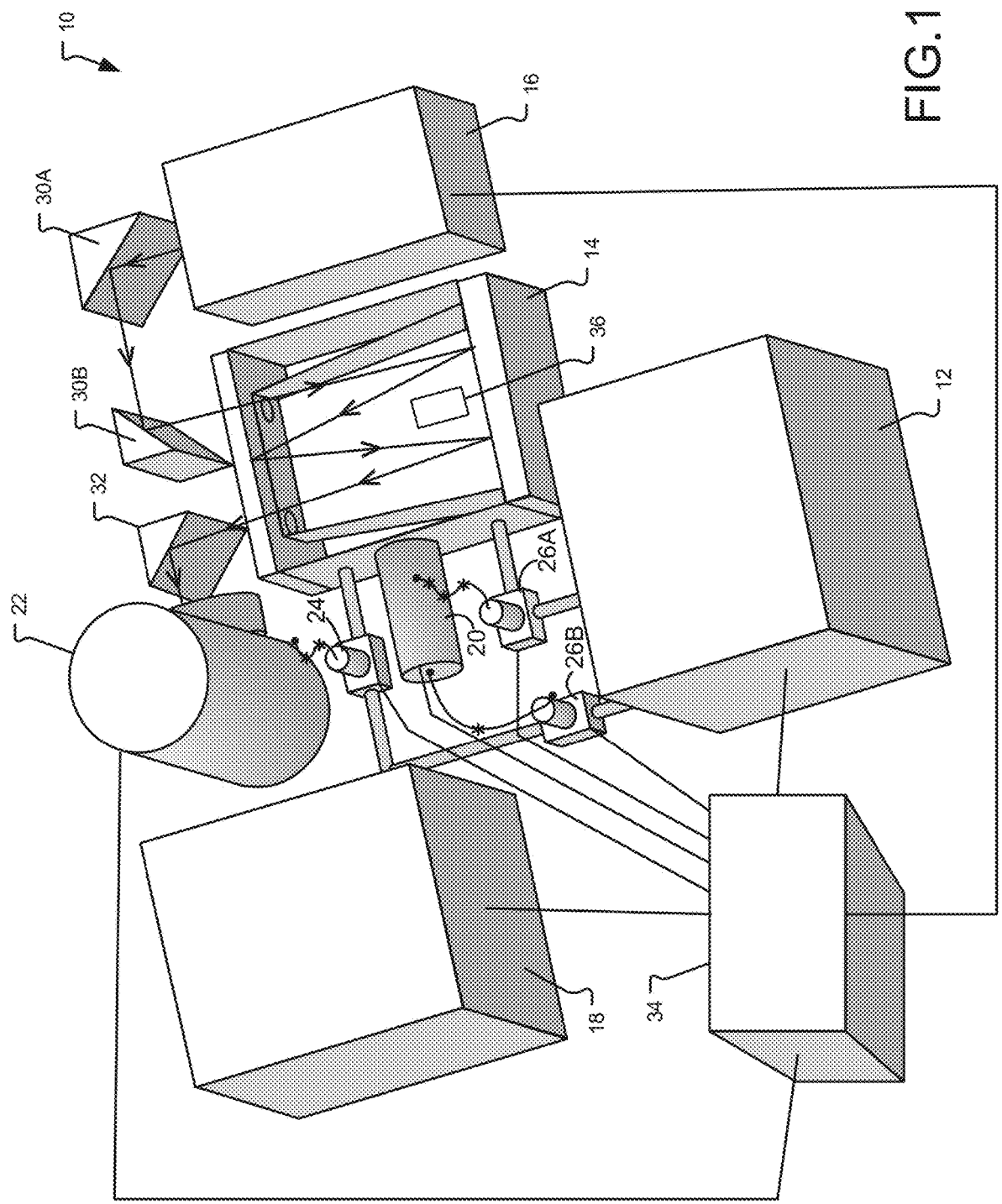
FIG. 1 is a schematic diagram of a sample analysis system, which is suitable for use with the present invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Embodiments described herein generally relate to spectroscopic techniques and, in particular, Fourier Transform Infrared (FTIR) techniques that can be utilized to identify unknown compounds present in a sample. These techniques are typically implemented by software executed by a computer and, in many cases, can be applied or adapted to any analysis process or instrumentation that uses FTIR spectrometry system or other spectrometry systems. In specific examples, the spectroscopic analysis is further enhanced or facilitated by a temporal separation of unknown compounds present in the sample being analyzed.

A suitable system and method that couple a time-resolved separator, e.g., a gas chromatograph (GC) or another suitable device, to an analyzer that relies on optical spectroscopic technology such as FTIR, is described in U.S. Pat. Appl. Pub. No. US 2015-0260695 A1, now U.S. Pat. No. 9,606,088 and U.S. Pat. Appl. Pub. No. US 2017-0122920 A1, these patent documents being incorporated herein by this reference in their entirety.

Generally, the system in the U.S. Pat. No. 9,606,088 is configured for analyzing a sample, typically a mixture containing more than one distinct chemical species. Components in the sample can be separated through various suitable techniques. A common temporally resolving separator is a GC column in which compounds in a mixture become separated based on their flow rates. Typically, lighter gases will elute through a column quicker than heavier ones. In a sample analysis system such as, for example, that described in U.S. Pat. No. 9,606,088, the GC column allows the FTIR system to differentiate substances with similar looking spectra using time. The electromagnetic-based radiation spectroscopic device (an FTIR spectrometry system, for example) can be used to identify and, in many cases, quantify the species present, resolved temporally by the separator. The coupling between separator and optical spectroscopic analyzer can be based on a sample cell that integrates the sample in the cell or the sample flows through the cell either continuously or non-continuously. Controls, automation instrumentation, computer interfaces, algorithms and/or software-related features also can be provided.

Shown in FIG. 1, for example, is a system 10, including a separator such as gas chromatograph (GC) 12, sample cell 14, and a spectrometer, e.g., FTIR or dispersive or tunable source spectrometer 16, which includes a light, and more generally, an electromagnetic (EM) radiation source. In specific implementations, GC 12 and/or FTIR spectrometer 16 are commercially available instruments, with exhaust from the GC being often directly coupled to the FTIR sample cell.

Some embodiments described herein can be practiced or adapted to other separator systems and other spectrometry systems beyond GC-FTIR. For example, the spectrometry system determines the spectral response of the components in the sample cell in one or more of the following spectral regions millimeter, microwave, terahertz, infrared (including near-, mid- and/or far-infrared), visible, ultraviolet (UV) (including vacuum ultraviolet (VUV)), x-rays and/or gamma. Further, the detection employed can measure different characteristics, such as absorption spectra, emission (including blackbody or fluorescence) spectra, elastic scattering and reflection spectra, impedance (e.g., index of refraction) spectra, and/or inelastic scattering (e.g., Raman and Compton scattering) spectra of the components in the sample cell 14.

In general, the GC uses a stationary phase, which is typically a microscopic layer of liquid or polymer on an inert solid glass or metal tube, i.e., a column. The mobile phase is a carrier gas, usually an inert gas such as helium or a non-reactive gas such as nitrogen. The carrier gas flow is controlled by flow controllers and/or a series of valves to maintain or vary the flow rate during the separation. The flow controllers and valves can also be used to allow the entire sample or a fraction of the sample to enter the column. The column is located in an oven where the temperature of the gas passing through the column can be controlled. The gaseous compounds interact with the walls of the column or stationary phase, causing each compound to elute at a different time, known as the retention time of the compound.

Carrier gases that can be used include nitrogen ($N_2$), for instance ultra-high purity (UHP) $N_2$, or another suitable gas or gas mixture as known in the art.

Typically, output from the separator, such as GC 12, is in a gaseous state, containing one or more gases and/or vapors. This output is directed to sample (also referred to as gas) cell 14.

In some examples, the cell 14 is a vessel that can be evacuated and configured to maintain a gas pressure lower than the surrounding (atmospheric or ambient) pressure to integrate the sample over time. In specific implementations, the pressure in the sample cell is within the range of about 0.001 to about 1.0 atm. For instance, a flow rate of 1 mL/minute, a sample cell volume of 200 mL and a starting gas cell pressure of ½ atmosphere can provide a 100-minute time period for data acquisition. This is considered a sufficient time window for most GC sample analyses. The pressure in the sample cell is reduced with a vacuum pump 18, or alternative apparatus capable of drawing a vacuum. The pressure in the sample cell can be monitored with a sensor, such as an absolute pressure sensor 20.

In other examples, the cell 14 is a partially integrating cell or a flow cell, such as a lightpipe, through which the output from the separator flows.

In one mode of operation, the sample flows through the gas cell 100 and out through the exit valve 94 and multiple spectra are obtained over time by the spectrometry system 60 and possibly averaged for detection limit reduction, i.e., enhancing detection sensitivity.

In some cases, no vacuum is required and the system can be operated at a suitable pressure. For instance, a compressor or column head pressure could be used to compress or flow the output from the GC into and possibly through the sample cell 14. Preferably, over pressurizing is avoided.

Sample cell 14 also receives electromagnetic radiation, for instance from light generated in FTIR arrangement 16 and can be designed to fit in the sample compartment of a commercial FTIR or other type of spectrometer. The cell is provided with optical components, such as windows that allow transmission of an electromagnetic radiation beam within a desired wavelength (or frequency) range into and out of the cell 14.

In the specific illustrated example, output radiation exits sample cell 14 and is directed by reflector 32 to detector 22, for instance a MCT (mercury cadmium telluride) device suitable for measuring the light in an FTIR. Specific examples employ liquid nitrogen cooled MCTs. One example of a suitable detector for a broad spectral analysis capability can be a 1 mm mid-band MCT with a cutoff of 16 µm.

System 10 includes electronics and computer systems and video displays and computer monitors for the computer systems. It can further include additional computer systems, devices, units, interfaces, data co-processors, and/or other components for data processing, analysis (including multivariate qualitative and quantitative), recording, reporting, equipment controls, automation, flow control and controllers, pressure sensors and controllers, heaters and temperature controllers, valves and vacuum generation technology, spectral libraries, and so forth. These components are generally indicated by reference numeral 34. One or more processors, memory devices, and so on, are provided in the computer systems for executing processes of the present invention.

Computer 34 in FIG. 1, and/or any associated components are configured for executing software for implementing embodiments of the present invention, allowing automated data handling and analysis based on processes described below and for generating a user interface for receiving input from users and display information to the users.

During operation, gas is captured in sample cell 14 for a specific time, based on the gas turnover rate in the sample cell. Various flow conditions can be employed. In a transient mode, for instance, the entire experiment (run) is conducted under a set, i.e., unchanging pressure, e.g., under a set vacuum pressure. In a full integration mode, sample cell 14 is evacuated and the sample is allowed to accumulate in the sample cell, with the pressure changing throughout the analysis. Also possible is a partial integration mode, where the sample cell is evacuated to a set pressure and a dilution gas is added and maintained in the cell for a period of time, e.g., 1 minute. Other operating modes can be employed, such as, for example, a mode that reduces the size of the data set. In other cases, a flow cell, such as a light-pipe, is employed. In the light-pipe or similar flow cell, the gas continuously flows through the cell with a characteristic residence time in the cell.

In some arrangements, a continuous carrier gas flow (e.g., $N_2$ or other suitable carrier gas) is directed from GC 12, into the sample cell. If desired, sample cell 14 can be closed to the $N_2$ flow from GC 12, for a given time interval. In yet other arrangements, the carrier gas, or the sample from the GC can be diverted to a secondary pumping service (not shown in FIG. 1) to prevent spectral interference from large concentration compounds such as solvent species. The flow can then be switched for sample collection. If pumping continues, the compounds that come off during this time will be standard chromatographic components (peaks) and their concentrations can be calculated as such. The peak will go up and go down as it enters and exits the sample cell so no further averaging will be done.

If sample cell 14 is initially evacuated, then sealed from pump 18, the carrier gas and sample components from the GC can accumulate in or flow through the sample cell and spectra can be obtained during the entire data collection. Since the chemicals are captured in the sample cell, the entire amount of each gas (compound) can be measured once it has completely eluted from the separation device (GC). Since the gas cell is a multiple pass gas cell in a one embodiment, there can be an increased absorption for each gas when compared to "light-pipe" system in an optimized design. By letting all the gas remain in the gas cell, this in effect integrates the sample peak from a traditional analyzer where the sample moves past or through the detection system. This integration provides a further enhancement in SNR, which can be a factor of 2 to 5 times since the entire amount of sample is measured once it has completely eluted. Typically, this improvement is dependent on the width of the eluted peak.

In specific implementations, a control circuit managed by the computer system 34 dynamically controls the sample cell pressure. For instance, automated valves can be set to pull a vacuum on sample cell 14 before starting a run or drawing the components through a flow cell. Pressure levels in the cell can also be controlled automatically. In many cases, isolating sample cell 14 from pump 18, thus allowing gas to accumulate in the sample cell, is also performed automatically. Automation can be used to set a desired carrier gas flow from the separator, e.g., GC 12, into the sample cell, to isolate the cell from the carrier gas, to divert the carrier gas to any secondary pumping station, to switch the flow to the FTIR gas cell for sample collection, and so forth.

With respect to data handling such as data collection and analysis, a process carried out in a system such as system 10 of FIG. 1 can involve data collection; data integral, differentiation or signal averaging; data spectral deconvolution/quantification; data reporting; among others. Computed data, plots generated by computer system 34, for instance, can be displayed in a graphical user interface of a display device of the computer system 34.

During operation, a sample is directed from the temporally-resolving separator to the sample cell, e.g., a gas cell that fully or partially integrates the components provided by the separator. The sample cell can be partially or fully evacuated and fluids such as gases and/or vapors are allowed to accumulate in the sample cell, effectively integrating their spectral signatures. Multiple spectra obtained over a time interval could then be averaged to best measure the integrated concentration in the sample cell. Obtaining a moving background that includes spectra from a previously eluted sample component, e.g., previously eluted chemical species, allows for the analysis of the current eluting components without interference from previously eluted components. The integrated and averaged multiple spectra can be corrected by using a similarly collected moving background, and the corrected data are compared to known spectra to identify one or more components, e.g., chemical species such as atoms, molecules, molecular fragments, ions, present in the sample component.

Data integral/differentiation/signal averaging functions can utilize, for instance, a 1 minute moving spectral average. Time spacing between background and sample spectrum can be varied. Data spectral deconvolution/quantification can be provided by a moving multiple linear regression based on compound retention index. A new regression matrix can be built for each spectrum analyzed in real time. Compounds selected for each regression are present for a relative distance +/– of its own retention index. Very high concentration components, internal standards or solvents can be present in a select set or in all regressions.

Typically, calibration data can be provided for each compound, and, in specific implementations at multiple concentrations. Retention index per compound can be determined using hydrocarbon reference standards or obtained from current mass spectral library data. For instance, retention index data are available from many sources, as known in the art, and are typically provided based on the type of column being utilized. Calibration data can be called when a certain index is reached, e.g., for the deconvolution operation. An initial prediction could be performed to determine which compounds within a retention index window might actually be present. This initial screening will limit the number of compounds then utilized in the multivariate analysis.

During FTIR sample analysis, peak structures observed in a sample spectrum are caused by substances absorbing IR light. These peaks are indicative of one or more compounds (often in gaseous or vapor form) being present in the sample. Most FTIR computer analysis algorithms are capable of selecting several compounds or combinations of compounds to analyze, for example, 2 to 20+ compounds or mixtures. The analysis can involve selecting a region of the spectrum to analyze each gas (where it absorbs). This step can be preset or selected by the computer system based on potential interferences. Multiple regions can be used for each compound to get more quantitative precision and a better qualitative prediction. For example, if a compound is known to have two absorption bands of equal strength and the sample spectrum includes one absorption band but not the other, the unknown cannot be the compound characterized by the two band of equal strengths.

Computer-related analysis techniques that can be used or adapted in practicing aspects of the invention are described in U.S. Pat. No. 9,606,088.

In one approach, a deconvolution algorithm executed by the computer system 34 is designed to analyze the resultant spectra to determine the chemicals present and their respective concentrations. In specific implementations, each gas to be analyzed has a stored calibration spectrum in the computer system that will be used to identify and quantify its presence. Known IR deconvolution algorithms can be used or adapted. Examples of suitable deconvolution techniques include but are not limited to those based on multiple regression analysis, linear or non-linear regressions, least squares analysis, partial least squares (PLS) analysis, inverse least squares analysis or other approaches.

Other tools that can be utilized include a mathematical matrix or matrices generated to analyze for each compound, with some instruments creating just a single matrix and analyzing all the gases simultaneously. Other instruments analyze each compound individually, so that the potential interferences are minimized and such that one compound does not affect the analysis of another. In yet other instruments a compound is analyzed in multiple regions and the results are compared to determine the true presence and concentration.

Once certain compounds are identified and quantified or potentially before spectral analysis as a prescreening technique, a goodness of fit, using, for instance, multiple spectral regions, can be performed to give the likelihood that the peaks observed in the collected spectra are the compound identified or compound in question. Reporting the compound can be accompanied by the percent likelihood that it is indeed the compound as part of the result. In many cases, a 95% or higher may indicate that the compound identified is the correct compound.

In many instances, the sample analyzed contains two or more compounds (gases). Identifying multiple compounds (more than 25 in some samples) from a single spectrum can pose software difficulties. For instance, having 25 unknowns requires 25 independent equations. In some cases, the number of unknowns is reduced by the fact that not every gas absorbs in the same spectral region, with maybe only a few absorbing at any one spectral location.

Since a technician may not know from the onset what compounds may be present in the sample, means for identifying likely compounds based on the visual peaks in the sample spectrum would be a desirable and useful tool in advancing the analysis. Even if the unknowns are not of direct interest, identifying them and including their spectra in regression may improve the accuracy for other gases being measured.

One approach in identifying which likely compounds may be present in the sample involves a "local" peak matching technique. In this approach, one sample peak is identified and compared to or "matched" against a reference library by the computer system 34.

The peak of interest, also referred to herein as the peak in the primary region, can be identified manually by the user or by another suitable method such as automatically by the computer system 34. Selecting the primary region can be based on what is already known about the sample, signal strength, experience, the identity of other compounds present and/or other factors.

Figure 2:
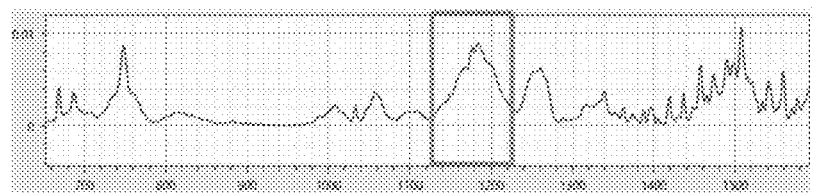
FIG. 2 is a plot presented in a user interface on a monitor of the computer system of the FTIR absorbance as a function of wavenumber of an unknown compound, highlighting the features in the 1130 to 1220 $cm^{-1}$ spectral region.

Shown in FIG. 2 is an illustrative FTIR spectrum (absorbance as a function of wavenumber). The highlighted peak (also referred to as "band" or "feature") from 1130 to 1220 cm$^{-1}$ corresponds to one peak of an unknown substance present in the sample.

Figure 3:
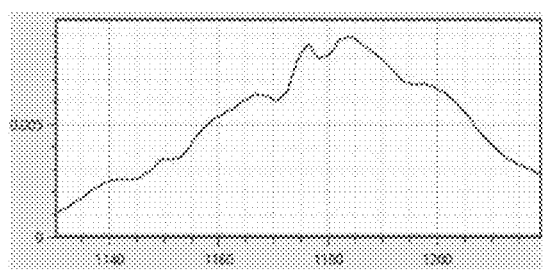
FIG. 3 is a plot of the isolated and clipped absorbance of the unknown compound of FIG. 2 in the 1130 to 1220 $cm^{-1}$ region.

Once the sample peak is selected (identified), it can be isolated (clipped) to eliminate other features in the larger spectrum, as seen, for example, in FIG. 3, showing only the primary peak region (1130 to 1220 cm$^{-1}$).

Figure 4:
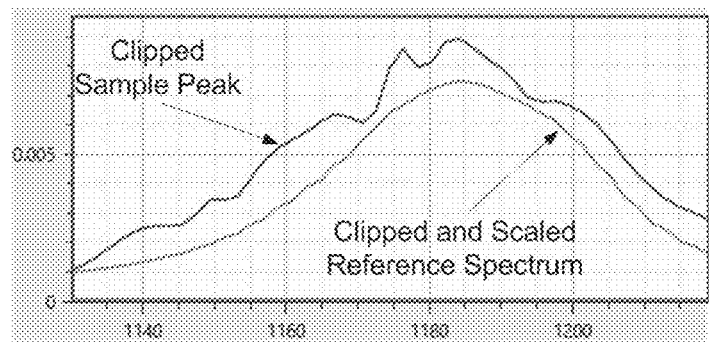
FIG. 4 is a series of plots of the absorbance of the unknown compound of FIGS. 2 and 3, and the scaled FTIR absorbance spectrum of a known reference compound in the 1130 to 1220 $cm^{-1}$ region.

Analysis software executing on the computer system 34, for example, selects reference compounds that have a similar peak structure from a reference library (database). The clipped sample region is regressed by the computer system 34 against each reference spectrum over the same wave number region, one reference spectrum at a time, for example. An illustration is found in FIG. 4 where the clipped sample peak (the unknown) is compared to a clipped and scaled reference spectrum (known) over the same wavenumber interval by the computer system 34.

Each regression fit has a goodness of fit metric calculated between the sample peak region and the reference compounds scaled by a regression scaling factor by the computer system 34. Those compounds that are above a certain goodness of fit threshold are presented to the user as an initial list of potential candidate compounds that could be present in the sample by the computer system 34 typically via a user interface generated by the computer system 34 and presented on a display device of the computer system 34. As used herein, "goodness of fit" refers to the statistic metric $R^2$ which is also known as the coefficient of determination.

Figure 5:
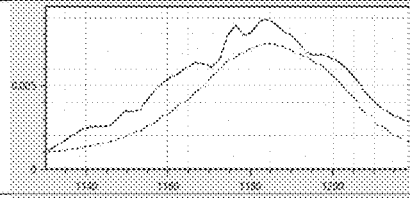
FIG. 5 is a series of fits between the FTIR spectral features in the 1130 to 1220 $cm^{-1}$ region of the unknown compound of FIGS. 2-4 and the scaled FTIR spectrum in the same spectral region of four reference compounds: acetamide-N—N-dimethyl, CAS Registry Number [127-19-5]; phenol, CAS Registry Number {108-95-2]; benzaldehyde, CAS Registry Number [100-52-7]; and isothiazole-4-phenyl, CAS Registry Number [936-46-9], which is presented in a user interface on a monitor of the computer system.
Figure 5:
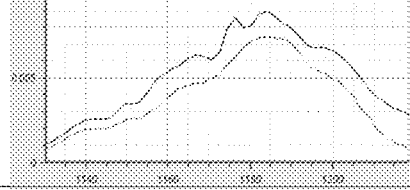
Figure 5:
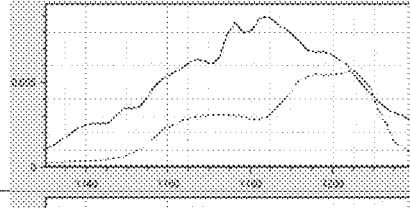
Figure 5:
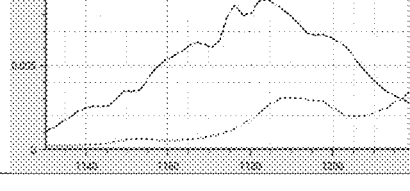

An example is presented in FIG. 5, where the clipped sample peak of FIG. 3 is compared (matched) by the computer system 34 to the following four reference compounds (scaled by the regression scaling factor): acetamide-N—N-dimethyl, CAS Registry Number [127-19-5]; phenol, CAS Registry Number {108-95-2]; benzaldehyde, CAS Registry Number [100-52-7]; and isothiazole-4-phenyl, CAS Registry Number [936-46-9]. A high goodness of fit is observed for the first two reference spectra (0.95562 and 0.94583, respectively). The goodness of fit for benzaldehyde is 0.50368 and that for isothiazole-4-phenyl 0.25008.

With techniques such as described in U.S. Pat. No. 9,606,088, the total number of possible candidates in the initial list can be further reduced by the computer system 34 using the information provided by or concerning a temporally-resolving separator, e.g., GC 12 in FIG. 1. This filtering process performed by the computer system 34 uses retention information associated with compounds that pass through the GC column.

As known in the art, compounds in a mixture can be separated by GC according to their flow rates through a column. The time needed by a given compound to pass through (elute) depends not only on the intrinsic nature of the compound (generally, lighter vapors elute faster than heavier ones, for instance) but also on external factors such as properties of the column (length, diameter, coating-related parameters, and so forth), carrier gas velocity, pressure, temperature, and so forth.

Since these and/or other variables are found to affect absolute retention times, GC analysis typically utilizes relative retention parameters, generally based on comparing the retention time of an unknown substance to that of a (known) standard compound. Expressing retention parameters in relative terms cancels out many operational effects such as, for example, column dimensions or carrier gas flow rates. Thus using the "retention index" of a certain organic compound, can normalize its retention time to the retention times of adjacently eluting compounds, in many cases adjacently eluting hydrocarbons, e.g., n-alkanes ($C_nH_{2n+2}$), and allows comparing values measured by different analytical laboratories under varying conditions. To illustrate, if pentane has a retention index of 500 and hexane a retention index of 600, isopropanol, with a retention index of 574, is expected to elute through the column between the times when pentane and hexane elute, after pentane and before hexane.

Mathematical relationships for determining retention indices have been developed for isothermal as well as temperature programmed CG and are known in the art. In the case of isothermal and non-isothermal (temperature programmed) GC, the Kovats retention index of an unknown compound, h, is given, respectively, by relationships (I) and (II) below:

$$I_x = 100_n + 100[\log(t_x) - \log(t_n)] / [\log(t_n+i) - \log(t_n)] \tag{I}$$

$$I_x = 100n + 100(t_x - t_n)/(t_{n+1} - t_n) \tag{II}$$

where $t_n$ and $t_{n+1}$ are retention times of the reference n-alkane hydrocarbons eluting immediately before and after chemical compound "X" and $t_x$ is the retention time of unknown compound "X".

In the case of isothermal analysis, if a logarithm of adjusted retention times or relative retentions of n-alkanes is plotted with carbon numbers, they will show a linear relationship. For temperature programming analysis, the peaks of n-alkanes appear at even intervals and the retention index obtained is known as linear retention index (LRI).

By analogy to Kovats indices, Lee indices characterize a series of compounds including benzene, naphthalene, phenanthrene and others. Tables of retention indices are available to help identify components by comparing an experimentally found retention index with known values. A computer system, e.g., computer 34 in FIG. 1, can include or can be connected to one or more libraries or database(s) that provide retention indices for a wide variety of compounds.

To determine when a compound will elute in a particular system (e.g., a specific lab or field instrument) retention indices (of universal use) are converted to retention times, employing, for instance, a set of compounds, often known as a "carbon ladder", with the goal of obtaining a system-dependent carbon ladder calibration.

The carbon ladder calibration is generated by running through the system, e.g., the system in FIG. 1, a known sample containing a set of hydrocarbon chains, e.g., alkanes such as pentane, hexane, heptane, octane, and so on. The hydrocarbons can be referred, respectively, as C5, C6, C7, C8, etc., depending on the number of carbon atoms in the chain. Lower and/or upper limits can be selected, as known in the art, based on experience, special circumstances, experimental determinations, and so on. In many cases, a suitable carbon ladder will include, for example, C5 through C15, C16, C17, C18 or higher.

For an initial run of the carbon ladder through the GC column, the time when each of the hydrocarbon peaks is recorded (as measured by a suitable detection means) gives rise to a chromatogram (generally a graph of the peak absorption over time). This is then used to convert retention indices into retention times. Thus, a chromatogram can be relied upon to identify when each hydrocarbon in the carbon ladder is peaking in a given system (associated with a given GC column) and hence to determine the retention time for each of the hydrocarbon in that system.

Linear interpolation techniques are employed for retention indices than lie between two known hydrocarbons. For example, if C5 (retention index of 500) is found to elute at 300 seconds and C6 (retention index 600) at 400 seconds, an unknown, also referred to herein as a "target" compound with a retention index of 550 is expected to elute half-way in between, with a retention time of 350 seconds.

Further methods have been developed to address difficulties arising in the detection and/or correct assignment of GC peaks. Examples include but are not limited to methods for removing solvent effects that can obscure carbon peaks in the chromatogram; "recovering" peaks that may not be immediately apparent; and/or techniques for determining goodness of fit or a similar parameter for increased confidence in the calibration. Details are provided in U.S. Provisional Patent Application No. 62/551,933, filed on Aug. 30, 2017, with the title Carbon Ladder Calibration, and U.S. Nonprovisional patent application Ser. No. 16/113,856, filed on Aug. 27, 2018, both of which being incorporated herein by reference in their entirety.

Applied to possible candidates that are above a goodness of fit threshold, reference compounds whose retention window does not match the retention time of the sample spectrum are eliminated. Typically, the retention window for eliminating some of the reference candidates that satisfy the FTIR goodness of fit criteria but not retention time criteria is selected based on the retention time of the sample unknown(s). In some cases, the filtering is performed using a window that is larger, by a small time, $\Delta t$, for instance, than the retention time of the sample unknown(s). Selecting a slightly larger retention window provides added confidence ensuring that potential candidates are not eliminated due to uncertainties caused by the calibration methods, instrumentation, user inputs, data interpretation, and so forth.

Figure 6:
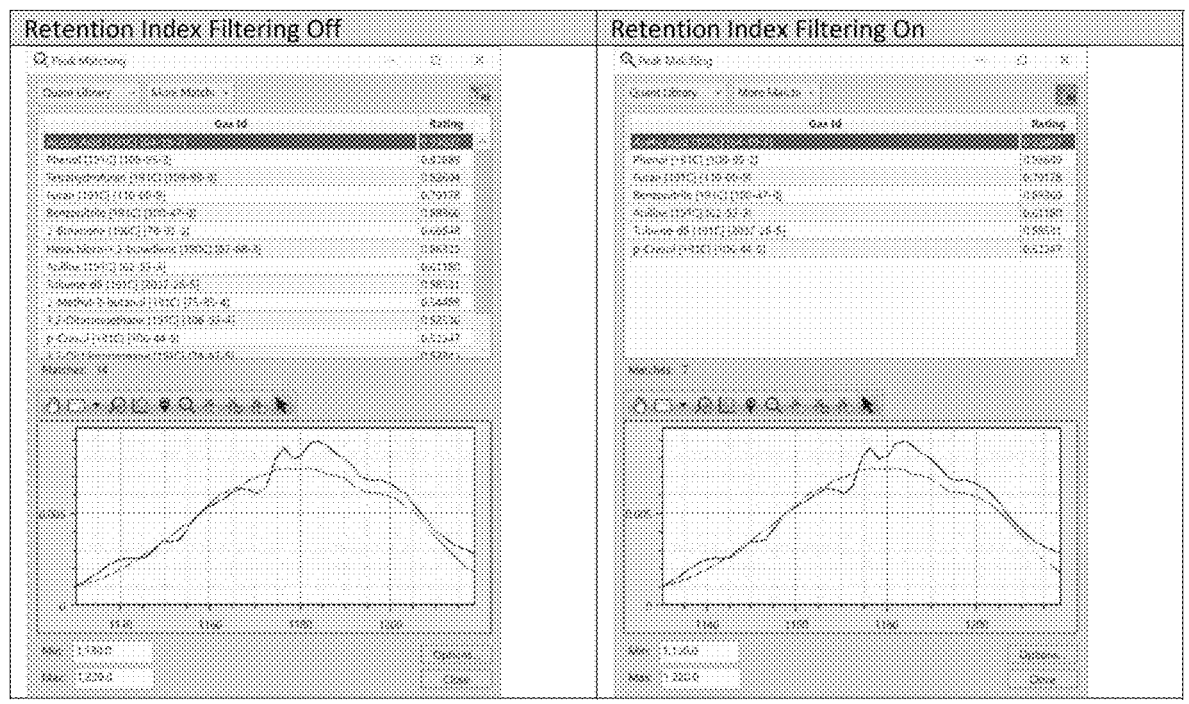
FIG. 6 is a series of screen displays of the user interface of the computer system showing a user interface generated by the computer system on a display device, the displays show the effects of further filtering of possible candidates by GC retention parameters.

An example of filtering based on retention index and/or retention time information for the reference compounds (vapors or gases) in a GC-FTIR system such as that shown in FIG. 1 is presented in FIG. 6. The total number of possible candidates based on the FTIR goodness of fit criteria in the local peak matching method described above (with no further filtering) is shown in the left-hand list. The "filtered" list at the right, obtained using Carbon Ladder Calibration techniques found in U.S. Provisional Application No. 62/551,933, Carbon Ladder Calibration, filed on Aug. 30, 2017 and U.S. Nonprovisional patent application Ser. No. 16/113,856, filed on Aug. 27, 2018, retains only those reference compounds that elute at the retention time of the sample spectrum being matched. Typical time windows selected to carry out the conversion between retention indices to retention times were in the order of seconds.

Techniques other than those described above can be used or adapted to apply retention index and/or retention time information to narrow down the number of potential reference compounds.

Figure 7:
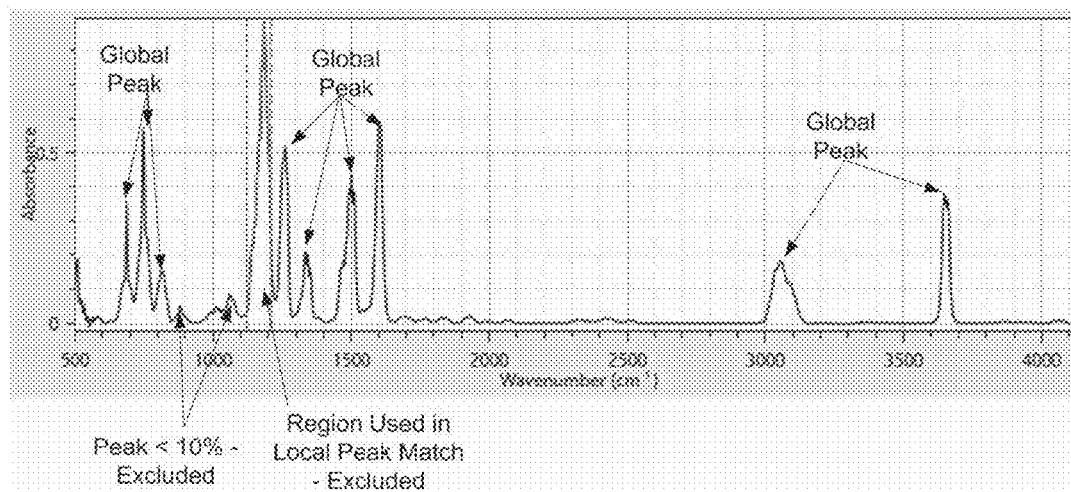
FIG. 7 is an absorbance FTIR spectrum of an unknown compound in the 500 to 4000 cm-1 spectral region, identifying local and global peaks.
Figure 8:
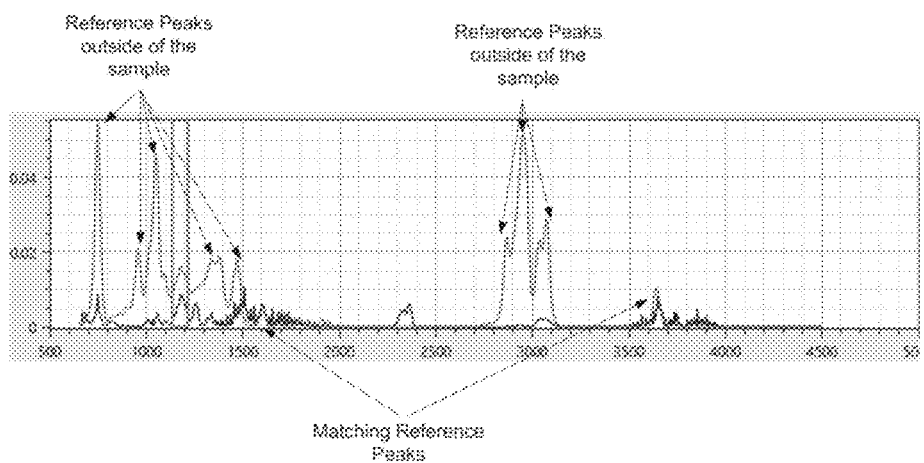
FIG. 8 is a superposition of FTIR spectral features of the unknown compound in FIG. 7 and scaled spectral features of a reference compound, identifying matching reference peaks and reference peaks extending outside the sample spectrum.

As seen in FIGS. 7 and 8, the feature discussed so far (in the 1130 to 1220 $cm^{-1}$ primary region) represents just one (small) region in the overall absorbance versus wavenumber FTIR spectrum of the (unknown) sample. One of the issues with "local" peak matching (namely, the analysis of just one feature or peak clipped from a larger FTIR spectrum), is that the list of possible candidate compounds can be long. For example, the EPA & NIST reference library of 5000+ gases would return 20+ matches for the 1130 to 1220 $cm^{-1}$ peak region being matched. Without retention index information, allowing the computer system 34 to filter the overall list, examining 20+ gases as possible matches can be time consuming. Even when retention times are available for added eliminations, situations presenting a large set of possibilities may still arise.

Techniques that can be utilized to further reduce or filter the number of potential candidates involve a "global" peak matching method. This method can be carried out by the computer system 34 alternatively or in addition to filtering based on retention index and/or retention time information.

Global peak matching focusses on features outside the primary matching region (e.g., outside the peak in the 1130 to 1220 $cm^{-1}$ region, in the example of FIGS. 2 and 3) and involves an assessment of how well features outside the primary region of reference spectra match the sample spectrum.

One embodiment of the global peak matching process begins with a list of reference spectra returned by the local peak matching algorithm. Each local peak match candidate can then be examined in more detail by the computer system 34.

Since information about the peak in the primary region has already been incorporated in the local peak matching approach described above, this peak can be excluded from the global peak matching analysis.

Minor peaks also can be excluded, by establishing a threshold, for example, so that only peaks above a certain signal level (e.g., absorbance level) become part of the global matching analysis. Excluding minor peaks addresses uncertainties in whether such peaks are truly indicative of a compound of interest, or mere artifacts due to impurities, noise, drifts and so forth.

In one example, the algorithm executed by the computer system 34 is set to identify only the peaks that are at least over 10% of the highest peak in the reference spectrum and to exclude the local peak in the primary region. This is illustrated in FIG. 7, identifying peaks in the primary region and "minor" peaks, both types being excluded from the global peak matching analysis. Also identified are the peaks included in the global peak matching process.

Typically, the reference spectra used belong to the possible candidates generated by the local peak matching technique descried above, optionally, filtered by retention time data. Each reference spectrum can be scaled, e.g., by the regression scaling factor computed for the local peak match.

The global peaks are evaluated against the sample spectrum. One embodiment in this evaluation considers two global peak matching criteria or rules:
whether the sample has a corresponding peak for the reference spectrum; and
whether the scaled reference peak extends outside of the sample spectrum.

The first rule is used by computer system 34 to increase confidence that the reference spectrum is a match, while the second rule is used to decreases confidence.

The light gray plot in FIG. 8, for example, corresponds to a reference spectrum, scaled by the appropriate scaling factor, e.g., as calculated in the local peak matching. Reference peaks that match as well as those outside the sample peaks illustrate the two rules above.

The two rules above are applied by adjusting the goodness of fit value calculated by the local peak fit either up or down depending on the rule being trigger. In doing so, the original goodness of fit metric ceases to be a pure goodness of fit. Rather, it can be thought of as a label or rating of the fit.

Further embodiments related to a global peak matching method, also referred to herein as "rule," that can be applied as follows.

In one example, the algorithm is designed to select a local neighborhood defined by an arbitrary frequency width, such as, for instance, 20 wavenumbers, on both sides of the peak) and regress that against the sample spectrum clipped to the same wave number region.

Figure 9:
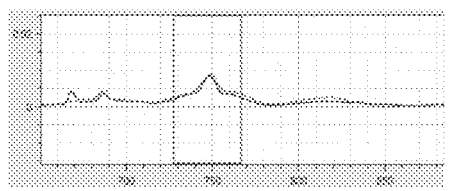
FIG. 9 is a superposition of a global peak in the FTIR absorbance spectrum of the unknown compound and a peak of a referenced spectrum in the same spectral region.

An illustration is shown in FIG. 9. This process can be the same as that used to match the primary region in the local peak match algorithm. In global peak matching, however, the matching region can be determined automatically by the neighborhood around the global peak.

A goodness of fit is calculated for that peak region. If the goodness of fit is "good" as defined as being greater than some goodness threshold or limit (set at 0.75 or another suitable level, for instance) then it is considered or allowed to boost confidence. A possible pseudo code can be:

```
rating = Local_Peak_GoodnessOfFit
For each peak
Spectrum global region = ReferenceSpectrum.ClipX(peak.X − 20, peak.X + 20);
GoodnessOfFit = Regression(sample, globalregion);
if (GoodnessOfFit > goodnesslimit)
    rating = rating * (1 +WeightedRamp(GoodnessOfFit, goodnesslimit,
```

1.0) / 20.0).

As seen below, WeightedRamp just normalized the input value (GoodnessOfFit) to have goodnesslimit map to 0 and 1.0 to map to 1.0 and the values in between map linearly:

```
double WeightedRamp(double val, double minr, double maxr)
{
if (val < minr)
    return 0;
if (val > maxr)
    return val;
if (PMath.ApproxEqual(maxr, minr))
    return 0;
else
    return (val − minr) / (maxr − minr);
}
```

In this approach, reference peaks with matches under the goodness limit have no contribution either positively or negatively to the outcome. One important reason for not using a "bad" fit to decrease the likelihood of the reference spectrum being a match is that the sample may contain other compounds (gases) causing interferences. In gas phase IR (and, in fact, any optical spectroscopy) absorbance spectra from multiple compounds typically add linearly to each other. Generally, if there are two gases absorbing in the same frequency range, each absorbance is independent or nearly independent of the other and what is obtained is the sum of the two spectra at each frequency.

Thus if the sample being analyzed contains other gases with spectral features in the same location as the global peak being evaluated, the matching region in the sample spectrum will be some linear combination of these multiple gas curves. This effect will produce a lower goodness of fit than if only one gas were to be present. Thus, the approach described here is designed not to infer from a bad peak match that a particular gas is not likely to be present.

A global peak mismatch rule also can be applied. This rule assesses how much a global peak in the reference spectrum extends beyond the peak in the sample spectrum. Basically, this rule indicates that there should be signal absorption found in the sample spectrum for these reference spectrum peaks even if the global peak matching rule can't see the peak structure.

So inside of the sample global peak loop, a negative weighting is tied to peaks that extend outside of the sample. Below is the pseudo code:

```
cmin = ReferenceSpectrum.MinimumY( );   // lowest wave number in spectrum
cmax = ReferenceSpectrumMaximumY( );   // highest wave number in spectrum
...
For each peak
...
    double cy = ScaledReferenceSpectrum.GetWaveValue(pt.X);
    double sy = sample.GetWaveValue(pt.X);
    // scaled reference spectrum peak is outside of the sample - ding rating
    if ((cy − sy) > 0)
    {
        rating *= 1.0 − 0.1 * PMath.WeightedRamp2(cy − sy, cmin, cmax);
    }
```

Figure 10:
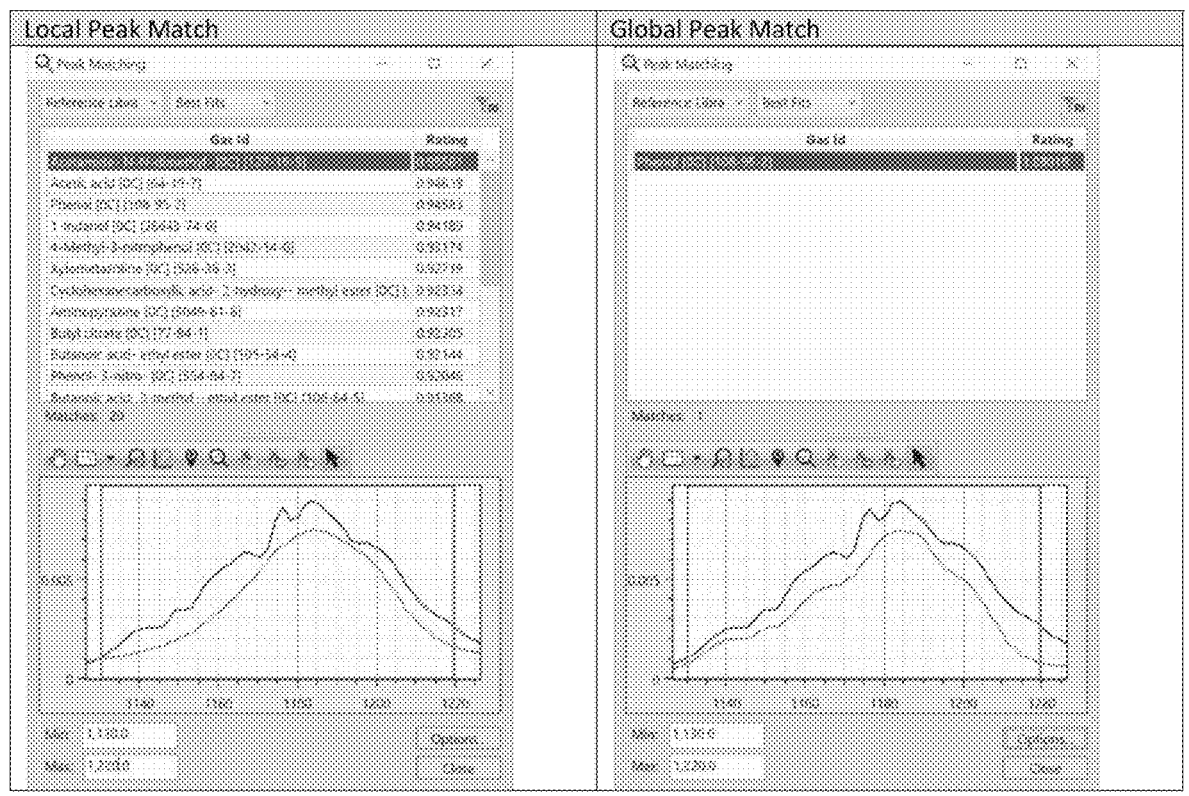
FIG. 10 is a screen display of the user interface of the computer system showing possible candidates generated by local peak matching (left) and one demonstrating the additional filter obtained by global peak matching (right).

Shown in FIG. 10 is a comparison of a local peak match vs. global peak match process. For the local peak match (left-hand side data), the actual compound (vapor) present, phenol, is not the best local match. Rather it has third highest rating, behind acetamide-N—N-dimethyl and acetic acid in a total of 20 initial possible matches. Once global peak features are included according to the global peak matching protocol described above, only one of the 5000+ possibilities in the NIST & EPA IR spectral gas phase data base can be considered a possible match.

Figure 11:
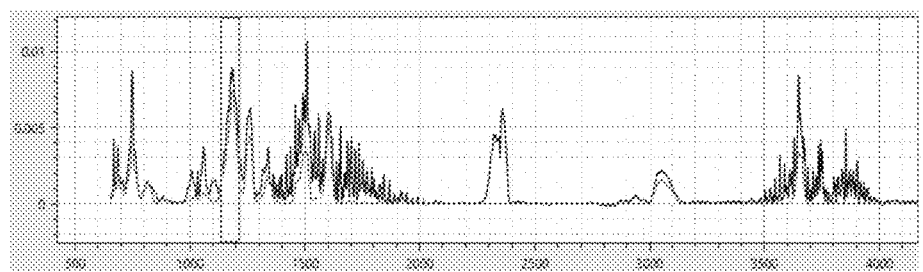
FIG. 11 is a fit between the absorbance as a function of wavenumber of the unknown compound and that of the known reference compound phenol over the same spectral region.
Figure 12A:
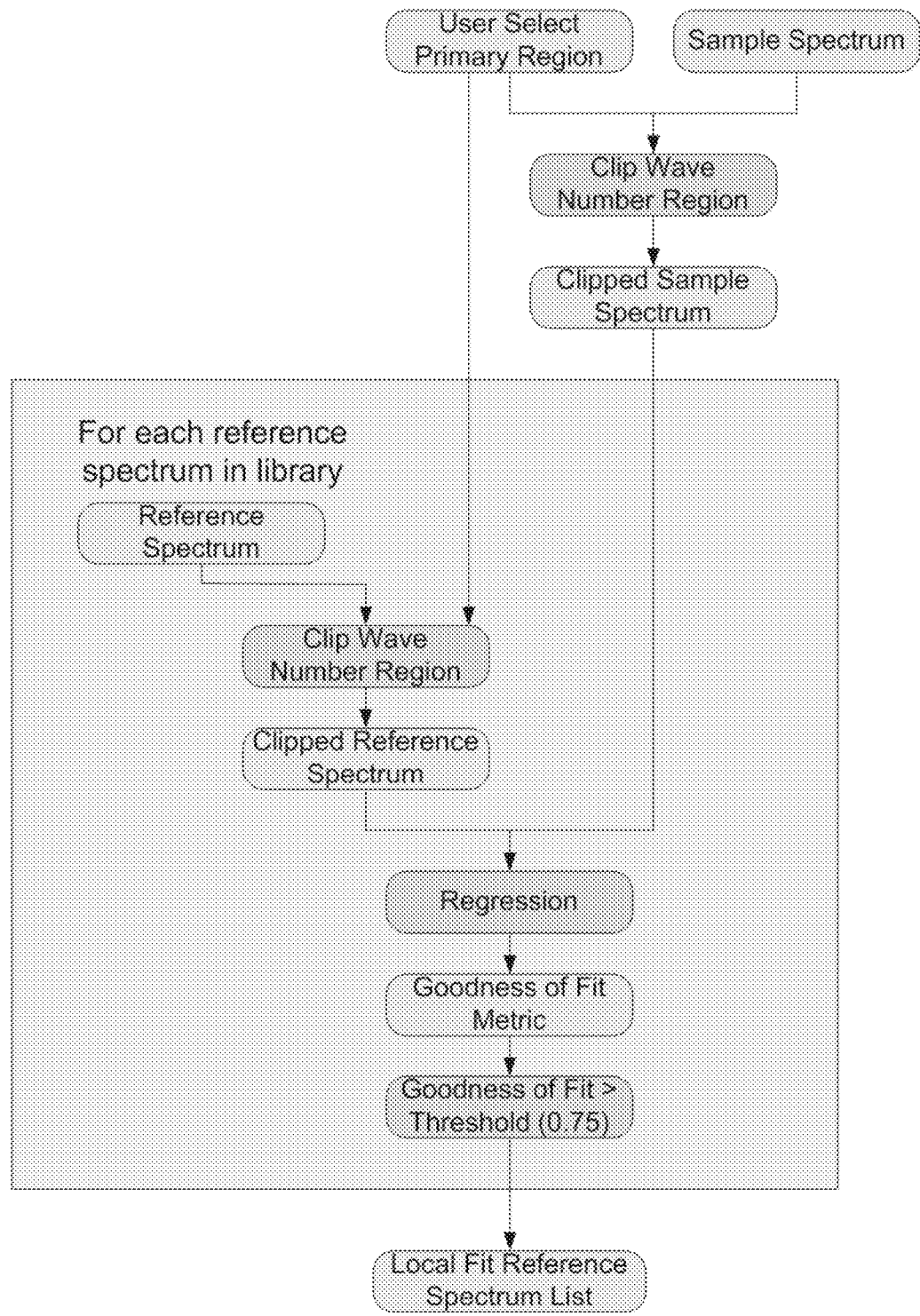
FIGS. 12A through 12D provide a flow chart of one embodiment of the process described herein.
Figure 12B:
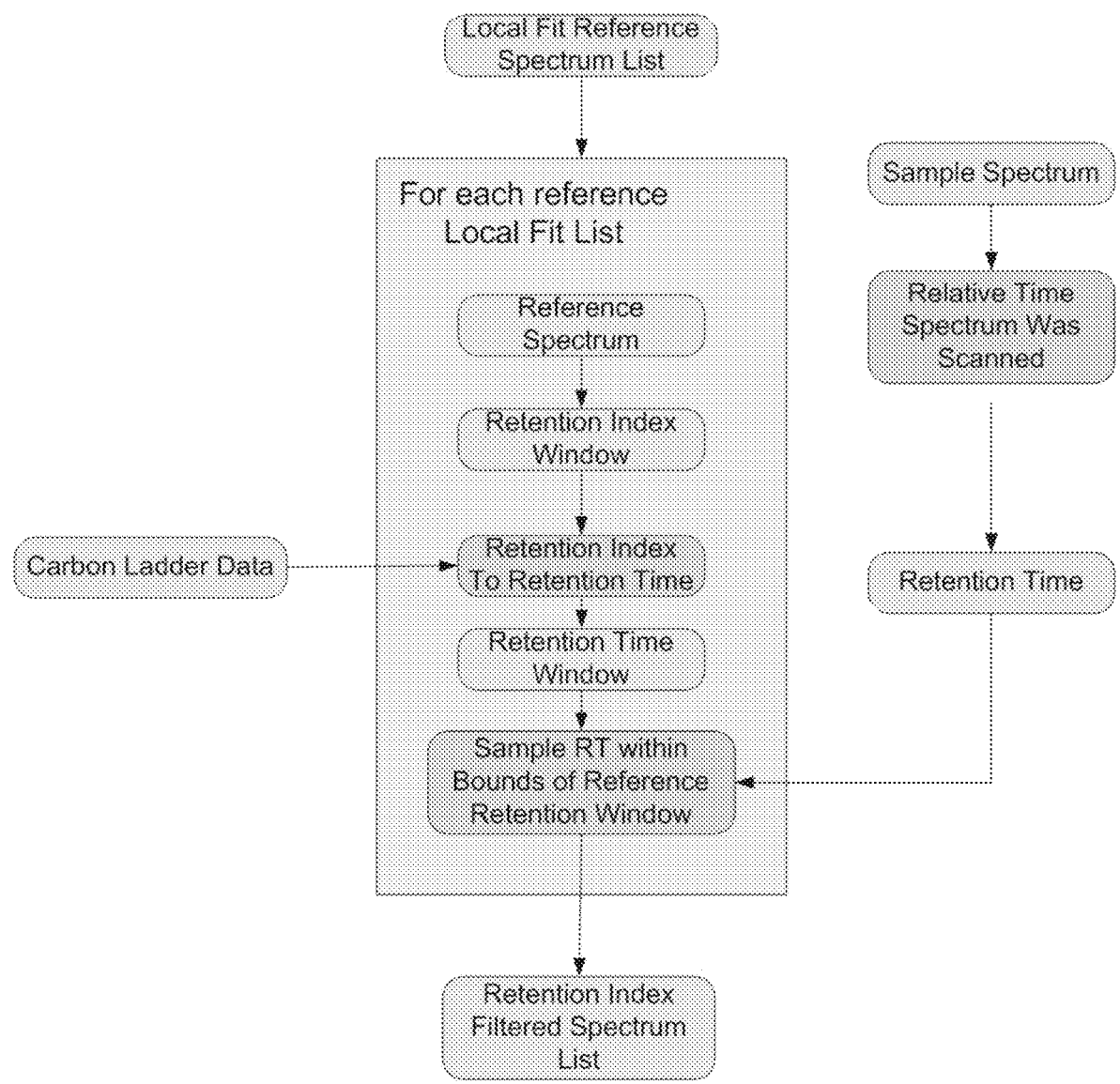
Figure 12C:
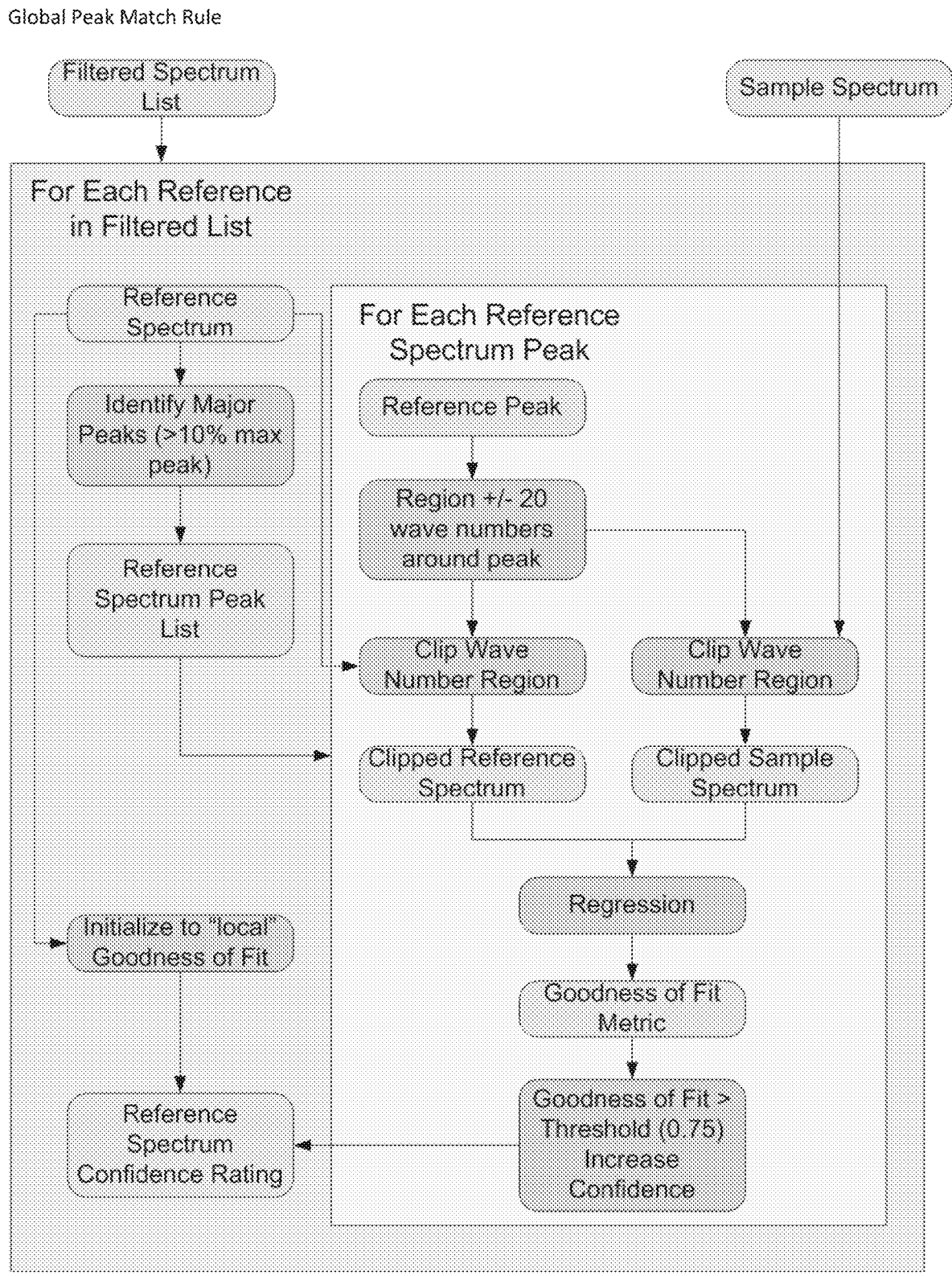
Figure 12D:
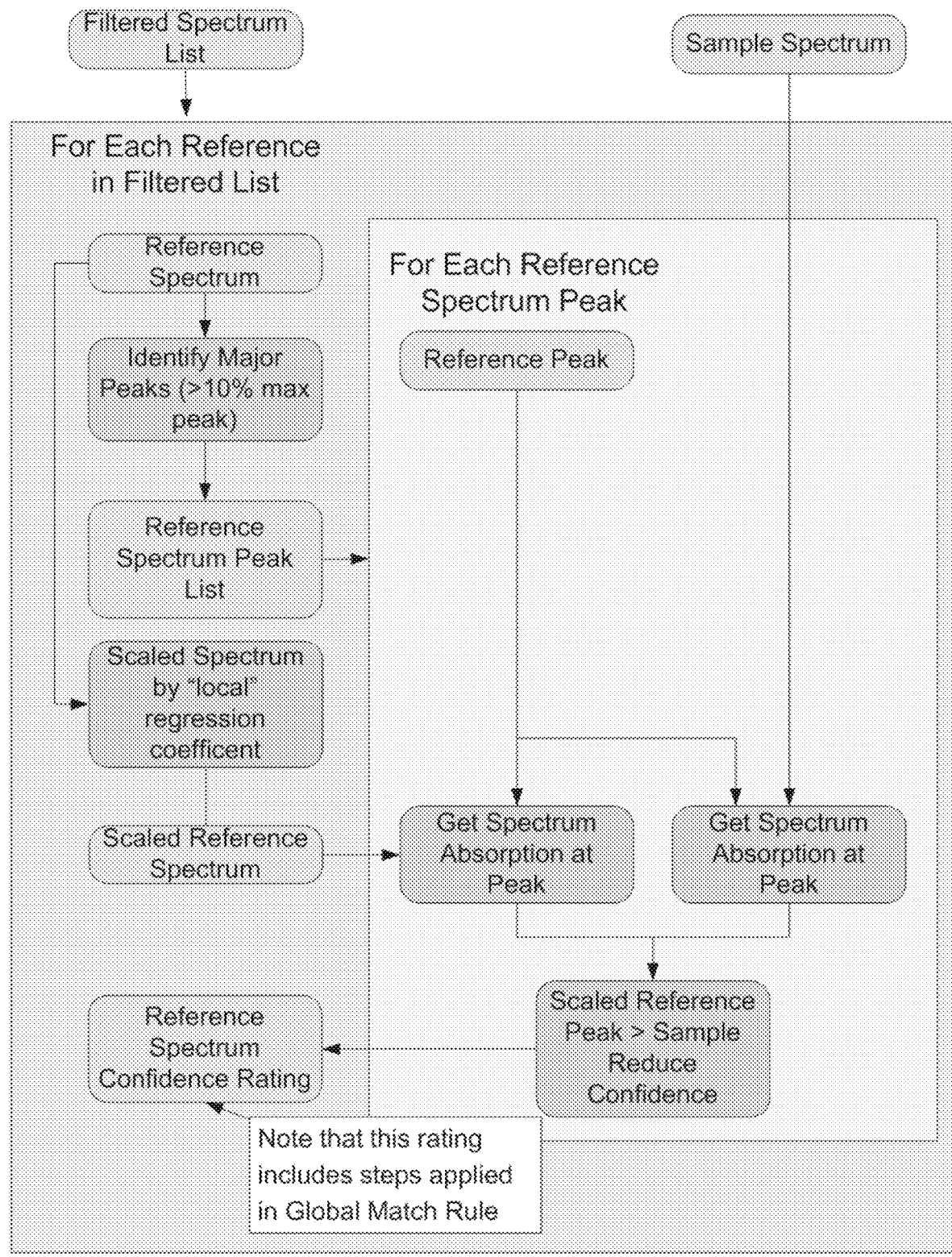

In the display of FIG. 11, the phenol spectrum (light gray) is superimposed over the entire sample spectrum (black). As seen in this figure, not all the peaks in the sample are explained by phenol nor do they need to be since other gases or vapors are present in the sample spectrum. Most of the phenol peaks are directly visible in the sample and no regions of the scaled phenol reference spectrum extend beyond the sample spectrum.

Presented in FIGS. 12A through 12D is a flow diagram of the steps performed to narrow possible candidates to one, phenol in the example above, includes local peak matching, GC retention time filtering, and global peak matching and mismatching.

While this invention has been particularly shown and described with references to preferred embodiments thereof, it will be understood by those skilled in the art that various changes in form and details may be made therein without departing from the scope of the invention encompassed by the appended claims.

What is claimed is:

1. A process for analyzing compounds in a sample, using a chromatography and Fourier transform infrared (FTIR) spectrometry system, the process comprising:
   selecting a primary FTIR region;
   a computer system performing a regression analysis on sample spectral features and reference spectral features in the primary region to generate a goodness of fit metric;
   the computer system applying a first goodness of fit threshold value to generate a list of potential candidates for the compounds;
   identifying a reference peak in a second FTIR spectral region that is outside of the primary FTIR region;
   the computer system performing a second regression analysis to generate a second goodness of fit metric for comparing the reference peak in the second FTIR spectral region with a corresponding spectral peak in the spectra of the potential candidates for the compounds; and
   eliminating from the list of potential candidates those candidates for which a second goodness of fit is below a second threshold value and those for which the reference spectrum peak, scaled by a regression coefficient, is greater than the corresponding spectral peak in the spectra of the potential candidates for the compounds.

2. The process of claim 1, wherein the list of potential candidates is reduced by gas chromatography retention time criteria.

3. The process of claim 1, further comprising eliminating from the list of potential candidates those for which a retention time determined by chromatography is outside a retention time window.

4. The process of claim 3, wherein the retention time window is determined by applying a carbon ladder calibration to reference retention indices.

5. The process of claim 1, wherein reference peaks having an intensity less than about 10% of a maximum peak intensity in the second spectral region are ignored.

6. The process of claim 1, wherein the reference peak in the primary region is ignored when identifying the reference peak in the second spectral region.

7. The process of claim 1, wherein no regions of a scaled reference spectrum extend beyond the sample spectrum.

8. The process of claim 1, wherein FTIR spectra are obtained using a multiple path sample cell or single pass cell or light pipe.

9. The process of claim 1, wherein the sample contains volatile organic compounds and inorganic compounds.

10. A chromatography and spectrometry system, comprising;
    a gas chromatography system for separating a sample into components;
    a spectrometry system for analyzing the components, and
    a computer system that performs a regression analysis on sample spectral features obtained using the spectrometry system and reference spectral features in a primary region to generate a goodness of fit metric, applies a first goodness of fit threshold value to generate a list of potential candidates, performs a second regression analysis to generate a second goodness of fit metric for comparing the reference peak in a second spectral region with a corresponding spectral peak in the spectra of the potential candidates, and eliminates from the list of potential candidates those candidates for which the second goodness of fit is below a second threshold value and those for which the reference spectrum peak, scaled by a regression coefficient, is greater than the corresponding spectral peak in the spectra of the potential candidates.

11. The system of claim 10, wherein the computer system reduces the list of potential candidates by gas chromatography retention time criteria.

12. The system of claim 10, wherein the computer system eliminates from the list of potential candidates those for which a retention time determined by chromatography is outside a retention time window.

13. The system of claim 12, wherein the retention time window is determined by applying a carbon ladder calibration to reference retention indices.

14. The system of claim 10, wherein the computer system ignores reference peaks having an intensity less than about 10% of a maximum peak intensity in the second spectral region.

15. The system of claim 10, wherein the computer system ignores the reference peak in the primary region when identifying the reference peak in the second spectral region.

16. The system of claim 10, wherein no regions of a scaled reference spectrum extend beyond the sample spectrum.

17. The system of claim 10, wherein the spectrometry system comprises a multiple path sample cell or single pass cell or light pipe.

18. The system of claim 10, wherein the spectrometry system is a Fourier transform infrared spectrometer.

19. The system of claim 10, wherein the sample contains volatile organic compounds and inorganic compounds.

* * * * *